United States Patent
Chow et al.

(10) Patent No.: US 10,473,581 B2
(45) Date of Patent: Nov. 12, 2019

(54) IRRADIATION OF LEAD BASED QUANTUM DOTS TO GENERATE NEAR INFRARED PHOSPHORESCENCE AS PART OF A COMPACT, THIN PROFILE, ON-DEMAND CALIBRATION SOURCE

(71) Applicant: Raytheon Company, Waltham, MA (US)

(72) Inventors: James R. Chow, San Gabriel, CA (US); Kalin Spariosu, Thousand Oak, CA (US); Stephanie Lin, Redondo Beach, CA (US); Kurt S. Ketola, El Segundo, CA (US); Tom Huang, Torrance, CA (US); Edward Ward, Jr., Redondo Beach, CA (US)

(73) Assignee: RAYTHEON COMPANY, Waltham, MA (US)

( * ) Notice: Subject to any disclaimer, the term of this patent is extended or adjusted under 35 U.S.C. 154(b) by 0 days.

(21) Appl. No.: 15/984,012

(22) Filed: May 18, 2018

(65) Prior Publication Data
US 2019/0049369 A1    Feb. 14, 2019

Related U.S. Application Data

(60) Provisional application No. 62/543,122, filed on Aug. 9, 2017.

(51) Int. Cl.
| | | |
|---|---|---|
| G01N 21/27 | (2006.01) | |
| G01N 21/35 | (2014.01) | |
| G01J 3/28 | (2006.01) | |
| G01N 21/359 | (2014.01) | |

(52) U.S. Cl.
CPC .......... *G01N 21/274* (2013.01); *G01J 3/28* (2013.01); *G01N 21/278* (2013.01); *G01N 21/35* (2013.01); *G01N 21/359* (2013.01)

(58) Field of Classification Search
CPC .......... G01N 21/274; G01N 21/35; G01J 3/28
See application file for complete search history.

(56) References Cited

U.S. PATENT DOCUMENTS

| | | | |
|---|---|---|---|
| 6,836,502 B2 | 12/2004 | Canady et al. | |
| 7,298,869 B1 * | 11/2007 | Abernathy | G06K 9/0063 324/323 |
| 8,733,702 B1 * | 5/2014 | Rawlings | B64C 23/005 156/230 |
| 9,312,662 B1 | 4/2016 | Larson | |
| 2002/0018632 A1 * | 2/2002 | Pelka | B82Y 10/00 385/130 |

(Continued)

FOREIGN PATENT DOCUMENTS

WO    2011050441 A1    5/2011

*Primary Examiner* — Marcus H Taningco
(74) *Attorney, Agent, or Firm* — Cantor Colburn LLP

(57) ABSTRACT

A light source, calibration device and method of calibrating an imaging device is disclose. The calibration device includes the light source which includes an ultraviolet light layer that, in operation, generates ultraviolet light, and a quantum dot layer that absorbs the ultraviolet light and, in response, generates radiation within the near infrared region at a selected intensity. The near infrared light is received at the imaging device and a sensitivity of the imaging device is altered to detect the near infrared light at the selected intensity provided by the light source.

18 Claims, 5 Drawing Sheets

(56) References Cited

U.S. PATENT DOCUMENTS

| | | | |
|---|---|---|---|
| 2009/0289199 A1* | 11/2009 | Hughes | B32B 41/00 |
| | | | 250/459.1 |
| 2009/0296368 A1* | 12/2009 | Ramer | F21V 14/003 |
| | | | 362/84 |
| 2011/0101848 A1* | 5/2011 | Cormier | G01N 21/278 |
| | | | 313/483 |
| 2015/0083933 A1* | 3/2015 | Eliason | H01L 33/06 |
| | | | 250/459.1 |
| 2016/0091367 A1 | 3/2016 | Micheels | |
| 2017/0200865 A1* | 7/2017 | Brummer | H01L 33/10 |

* cited by examiner

IRRADIATION OF LEAD BASED QUANTUM DOTS TO GENERATE NEAR INFRARED PHOSPHORESCENCE AS PART OF A COMPACT, THIN PROFILE, ON-DEMAND CALIBRATION SOURCE

CROSS-REFERENCE TO RELATED APPLICATIONS

This application takes priority from U.S. Provisional Application Ser. No. 62/543,122, filed on Aug. 9, 2017, which is incorporated herein in its entirety by reference.

BACKGROUND

The present disclosure relates generally to an apparatus and methods for calibrating an imaging device and, in particular, to an apparatus and method for providing radiation within a near infrared light band of frequencies for calibration purposes.

Imaging devices are used in a variety of platforms (terrestrial, airborne, space, etc.) to take images of ground locations at hyper-spectral electromagnetic radiation frequencies, such as ultra-violet (UV) frequencies, visible (Vis) light frequencies, near infrared (NIR) frequencies, short wave infrared (SWIR) frequencies, medium wave infrared (MWIR) frequencies, and long wave infrared (LWIR) frequencies, etc. These imaging devices require scheduled or periodic calibration using hyperspectral calibrators. Traditional hyperspectral calibrators can be problematic for use in resource-constrained platforms such as space platforms because they can take up a significant portion of the volume and weight of the platform, and require continuous power in order to provide accurate and repeatable frequency and radiant power during the calibration process. Traditional bulbs used in integrating spheres for visible, NIR and SWIR calibration devices tend to suffer from mechanical fatigue and fracture after cycling on and off over thousands of cycles, thereby requiring the platform to carry multiple bulbs for reliable mission completion. For calibrations that utilize the solar reflection off of a diffuse reflector, additional equipment is required to monitor the degradation of the spectral properties of the reflector. Such equipment therefore requires additional volume and weight from an already resource-constrained platform.

SUMMARY

According to one embodiment, a method of calibrating an imaging device includes: generating ultraviolet light at an ultraviolet light layer of a multi-layer light source, absorbing a portion of the ultraviolet light at a quantum dot layer of the multi-layer light source, wherein the quantum dot layer generate near infrared light at a selected intensity, receiving the near infrared light at the selected intensity at the imaging device, and altering a sensitivity of the imaging device to detect the near infrared light at the selected intensity provided by the light source.

According to another embodiment, a light source includes: an ultraviolet light layer that, in operation, generates ultraviolet light; and a quantum dot layer that absorbs the ultraviolet light and, in response, generates radiation within the near infrared region at a selected intensity.

According to yet another embodiment, a calibration device includes: an ultraviolet light layer that, in operation, generates ultraviolet light; and a quantum dot layer that absorbs the ultraviolet light and, in response, generates radiation within the near infrared region at a selected intensity.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

For a more complete understanding of this disclosure, reference is now made to the following brief description, taken in connection with the accompanying drawings and detailed description, wherein like reference numerals represent like parts.

DETAILED DESCRIPTION

As discussed above, calibration equipment can require a significant amount of the platform's limited size, weight and power (SWaP) budget. Disclosed herein is a calibration source that requires, in one embodiment, a smaller size and weight compared to prior bulb-centric systems, utilizes significantly less average power, and provides high reliability as well. In one embodiment, a calibration source that includes various layers of material, each layer providing light at wavelengths particular to the material of the layer, is described. The calibration source may, in one embodiment, take up a small volume and have low power requirements. The calibration source can sustain more on/off cycles than a calibration source using a filament bulb. While the calibration source can be used in many applications, the longevity of the calibration source allows it to be used in extreme environments. In one embodiment, the calibration source can be placed onboard a satellite orbiting the earth or on an airborne vehicle. The calibration source provides near infrared light that can be used during flight to calibrate imaging devices that are onboard the satellite or airborne vehicle.

In an operation, the calibration device provides a light source of near infrared light. The near infrared light is provided by a stack of thin layers of materials, which can include: a first layer having a first material that in operation generates ultraviolet light; a second layer having a second material that absorbs, in part, the ultraviolet light from the first material and, in response, generates visible light; and a third layer having a third material that absorbs the ultraviolet light passing through the second layer and the visible light from the second layer and, in response, generates radiation within the near infrared region ("near infrared light"). The near infrared light can be provided to an imaging device that outputs an image in order to calibrate the imaging device. Based on a calibration of the imaging device using the near infrared light, data obtained from the operation of the imaging device can be adjusted to accommodate changes in a spectral-radiant response of the imaging device resulting from the calibration of the imaging device.

Light takes up a region of the electromagnetic spectrum that is generally defined from a region of ultraviolet light to a region of infrared light. For purposes of discussion, ultraviolet light ("UV light") includes electromagnetic radiation having wavelengths within a range from about 10 nanometers (nm) to about 400 nm. Visible light includes radiation having wavelengths within a range from about 400 nm to about 700 nm. Near infrared light ("NIR light") includes radiation having wavelengths within a range from about 700 nm to about 1000 nm.

Figure 1:
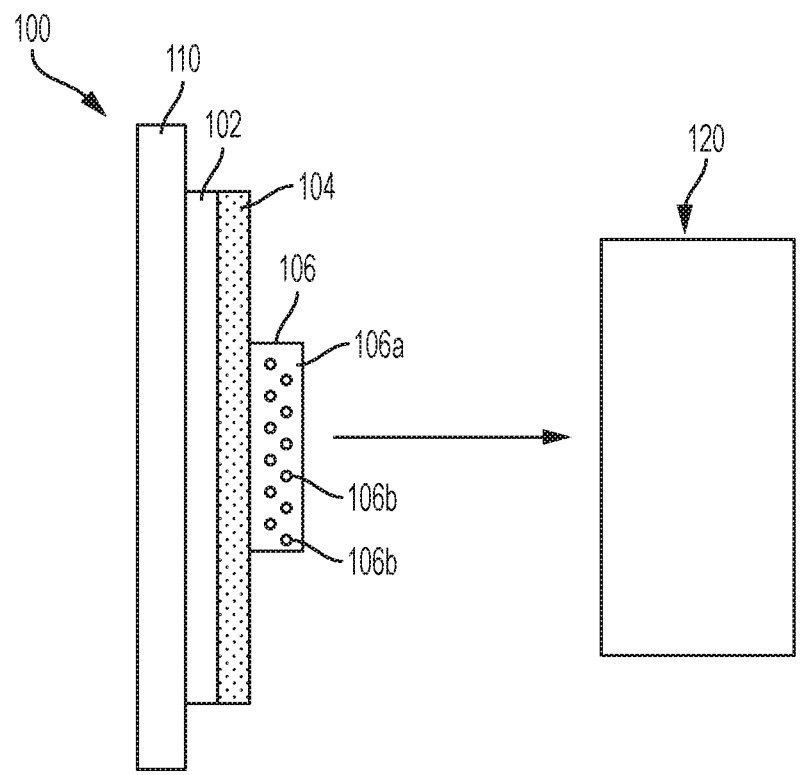
FIG. 1 shows a side view of a light source that provides near infrared light suitable for calibrating an imaging device, in one aspect of the present invention.

FIG. 1 shows a side view of a light source 100 that provides NIR light suitable for calibrating an imaging device 120 in one aspect of the present invention. The calibration device 100 includes a mounting substrate 110 upon which is formed one or more thin-film layers 102, 104 and 106. Each thin film layer 102, 104 and 106 provides light over a specified spectrum of frequencies. While three film layers are shown, more or fewer layers can be used. The mounting substrate 110 includes electrical connections for receiving electrical power and distributing electrical power to a first layer 102. The first layer 102 is formed on top of the mounting substrate 110 and is electrically connected to the mounting substrate 110. In one embodiment, the first layer 102 is in direct contact with the mounting substrate.

The first layer 102 ("ultraviolet light layer") includes a first material that generates ultraviolet light in response to the electrical power provided from the mounting substrate 110. In one embodiment, the first layer 102 includes one or more LEDs that generate radiation in the ultraviolet region of the electromagnetic spectrum ("UV light") in response to an electrical current.

A second layer 104 ("phosphor layer") of material is formed on the first layer 102. The second layer 104 may be attached directly to the first layer 102 or may adhere to the first layer 102 by an adhesive agent between the second layer 104 and the first layer 102 that is, at least in part, transparent to UV light. The second layer 104 includes a second material that absorbs UV light generated by the first layer 102 and emits visible light in response to the UV light. In one embodiment, the second layer 104 includes a layer of phosphors. Phosphors include materials that exhibit luminescence, including phosphorescent materials and fluorescent materials. Phosphors are often transition metal compounds or rare earth compounds of various types. The phosphors can be dispersed homogeneously through a matrix that forms the second layer 104.

A third layer 106 ("quantum dot layer") is formed on the second layer 104 so that the second layer 104 is between the first layer 102 and the third layer 106. The third layer 106 may be attached directly to the second layer 104 or may adhere to the second layer 104 via an adhesive agent between the third layer 106 and the second layer 104 that is, at least in part, transparent to visible light. The adhesive agent between the third layer 106 and the second layer 104 can also be transparent, at least in part, to UV light. The third layer 106 includes a third material that absorbs the visible light from the second layer 104 and generates near infrared light in response to the visible light. The third material can also absorb UV light from the first layer 102 that passes through the second layer 104 and generate the near infrared light in response to the UV light. In one embodiment, the third layer 106 includes a matrix material 106a that includes quantum dots 106b encased therein. The matrix material can be polymeric in nature such as a matrix of acrylate urethanes, in various embodiments.

Quantum dots (QD) are very small semiconductor particles that are several nanometers in size. The optical and electronic properties of quantum dots can be controlled by controlling their size and shape. In one embodiment, the quantum dots 106b of the third layer 106 are lead sulfide (PbS) quantum dots. In alternate embodiments, the quantum dots can include lead selenide (PbSe), Cadmium Sulfide (CdS), Cadmium-Tellerium-Selenide (CdTeSe) or any combination of PbS, CdS, PbSe, and CdTeSe. The quantum dots 106b absorb the visible light from the second layer 104 and generate MR light in response. In various embodiments, the quantum dots 106b can also absorb UV light from the first layer 102 and generate NIR light in response. Therefore the quantum dots of the third layer 106 can generate NIR light upon absorbing visible light from the second layer 104, UV light from the first layer 102 or a combination of the visible light and the UV light. The MR light generated by the dots 106b in the third layer 106 is directed towards the imaging device 120 for calibration of the imaging device 120.

Figure 1A:
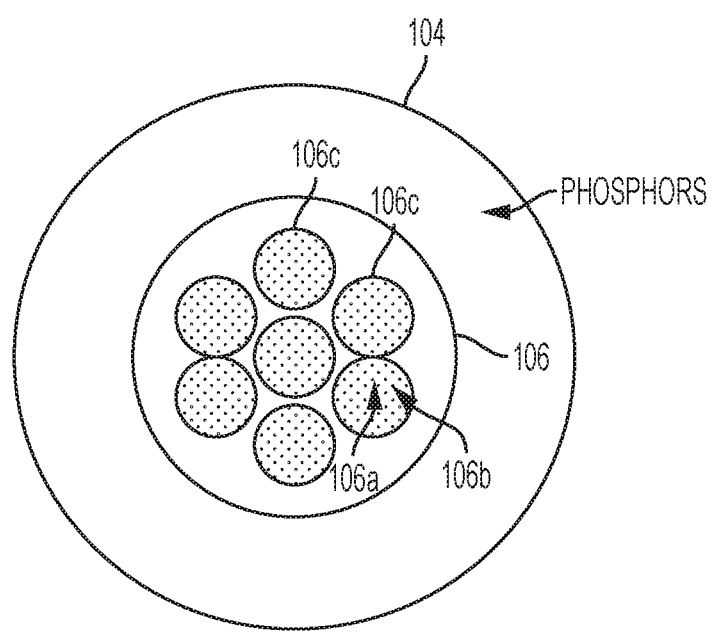
FIG. 1A shows a face-on view of the light source of FIG. 1.

FIG. 1A shows a face-on view of the calibration light source 100 in an embodiment of the present invention. FIG. 1A shows specifically the second layer 104 and the third layer 106. The second layer 104 includes the phosphors dispersed in a homogenous matrix. The third layer 106 shows an arrangement of including a plurality of cells 106c, with each cell 106c including the matrix material 106a and quantum dots 106b. The cells 106c are arranged in a hexagonal pattern. However, this arrangement of cells 106c is not meant to be a limitation of the invention, and any suitable arrangement of cells can be used. In addition, the third layer 106 may include a single thin film that covers the second layer 104, as shown in FIG. 1.

Figure 2:
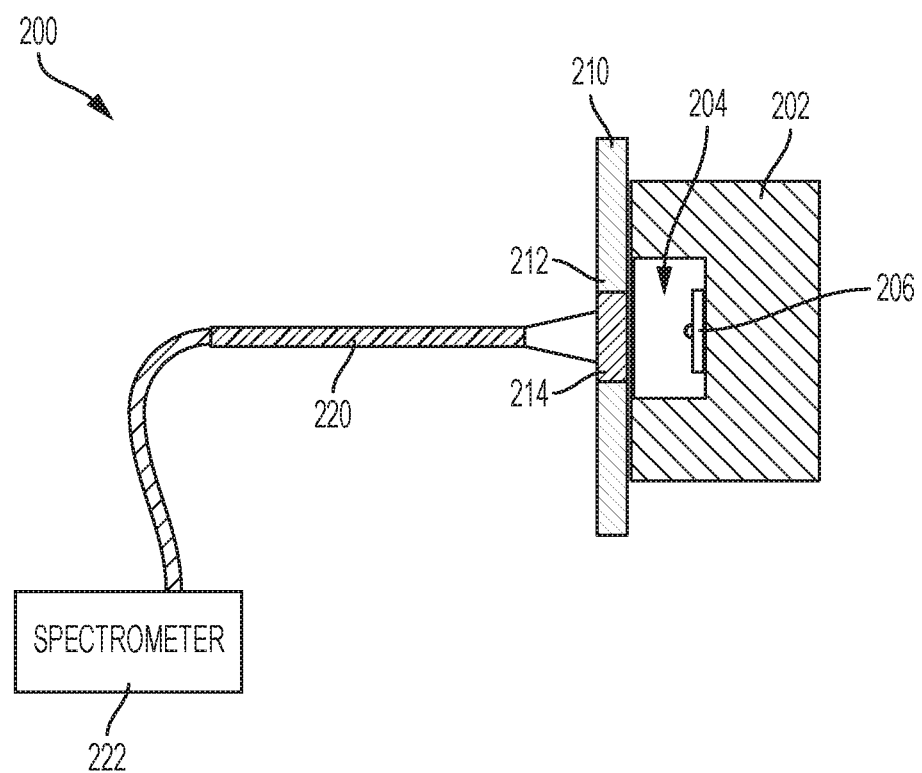
FIG. 2 shows a radiance measurement system for designing layers of the calibration device of FIG. 1.

FIG. 2 shows a radiance measurement system 200 for designing layers of the calibration device 100 of FIG. 1. The system 200 provides a base 202 having a cavity 204. One or more LEDs 206 are oriented in the cavity 204 in a direction so as to radiate electromagnetic energy out of the cavity 204. The base 202 includes electrical connections for receiving electrical power and distributing electrical power to the one or more LEDs 206. In various embodiments, the one or more LEDs 206 generate UV light.

A cover 210 is placed along a side of the base 202 that includes the cavity 204. The cover 210 has a hole 212 there through that is placed over the cavity 204 when the cover 210 is placed alongside the base 202. In an embodiment, the cover 210 can be secured to the base 202. A selected material 214 for calibration is placed within the hole 212. The hole 212 can be designed to support the shape of the selected material 214. The selected material 214 can be a phosphor layer or a quantum dot layer or a combination of both.

A cable 220 that can be optical cable or other light guide receives the light from the selected material 214 and directs the received light to a spectrometer 222. The spectrometer 222 measures the spectrum of the selected material 214. The spectrometer measurements can be used to adjust the calibration source, such as by adjusting a current supplied to the one or more LEDS 206, to select an optimal layer thickness, to select a material composition, etc. The spectra of various selected materials is discussed below with respect to FIGS. 3-4.

Figure 3:
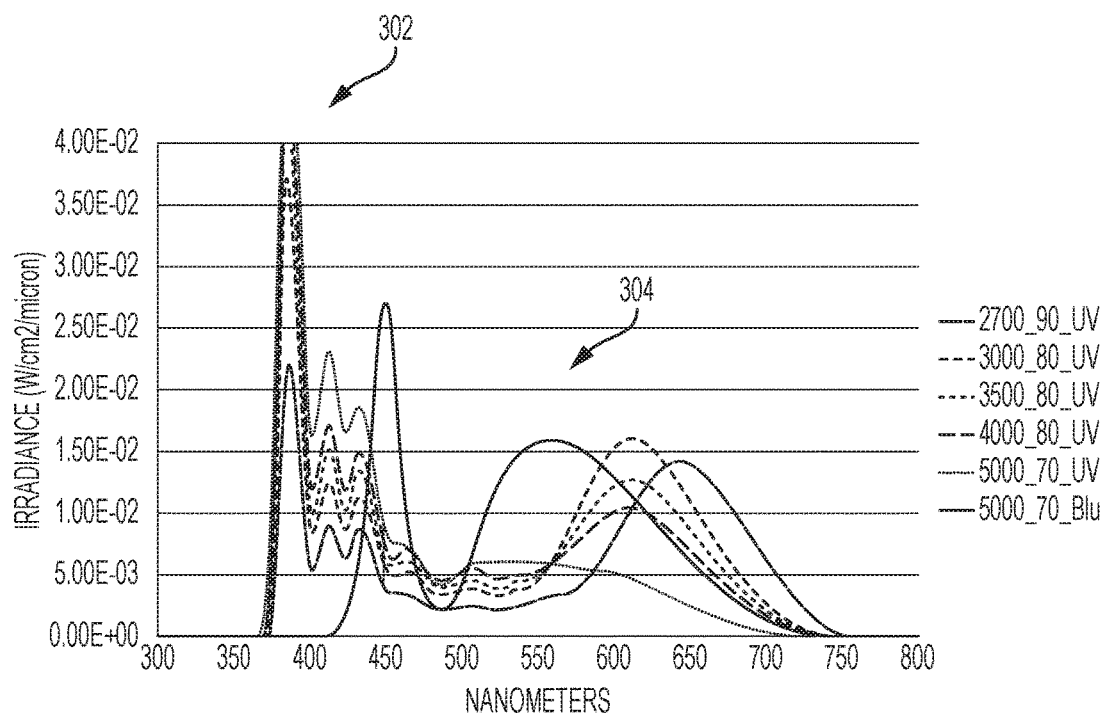
FIG. 3 shows spectra obtained at a spectrometer of the radiance measurement system for a layer of phosphors.

FIG. 3 shows overlaid spectra obtained at the spectrometer 222 for several different visible phosphor layers. Light from the ultraviolet LED shows peaks in the UV region 302. Light from the different phosphor layers shows a distribution of peaks extending from the UV to the visible light region 304.

Figure 4:
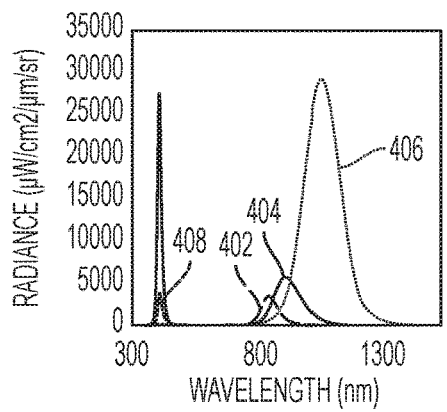
FIG. 4 shows spectra obtained at the spectrometer of the radiance measurement system for a layer of quantum dots encased in a polymeric matrix.

FIG. 4 shows spectra obtained at the spectrometer 222 for a layer of quantum dots 106b encased in a polymeric matrix material 106a. The LED power is at 15 W for these layers, which is about 70% of maximum LED power. Spectra are shown for a layers having spectral emissions at 800 nanometers (nm) (spectrum 402), 860 nm (spectrum 404), and 1000 nm (spectrum 406). A near UV spectrum peak (408) is shown for the UV light that is not absorbed by the layer of quantum dots 106b. The emission spectrum 406 peaking at 1000 nm has the largest peak and the peak lies within the NIR region.

Figure 5:
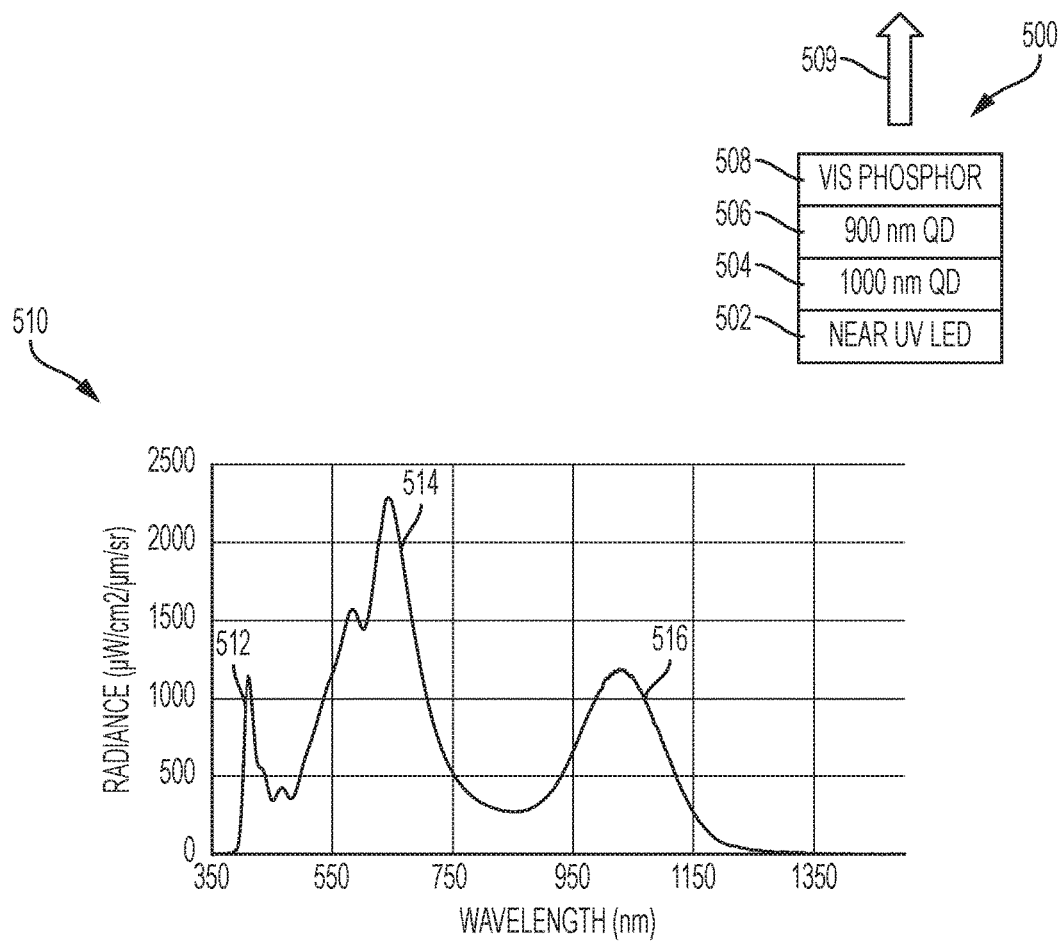
FIG. 5 shows a light source in another embodiment an emission spectrum generated by the light source.

FIG. 5 shows a multi-layered light source 500 and an emission spectrum 510 generated from the stack in another embodiment. The stack includes a first layer 502 ("ultraviolet light layer") including a near UV light source emitting UV light having a peak at about 405 nm. A second layer 504 ("first quantum dot layer") is stacked on top of the first layer 502 and includes a layer of quantum dots within a matrix in which the quantum dots emit a spectrum of light having a peak at about 1000 nm (in the near infrared region). A third layer 506 ("second quantum dot layer") is stacked on top of the second layer 504 and includes a layer of quantum dots within a matrix in which the quantum dots emit a spectrum of light having a peak at about 900 nm. A fourth layer 508 ("phosphor layer") is stacked on top of the third layer 506 and includes a layer of phosphor material emitting a visible spectrum of light. The near UV light from the first layer 502 is received at the second layer 504. The 1000 nm quantum dots of the second layer 504 absorb a portion of the near UV light and emits light at 1000 nm. The 1000 nm light emitted from the second layer 504 passes through the third layer 506 and fourth layer 508 without absorption. Similarly, a portion of the near UV light that passes through the second layer 504 is absorbed by the third layer 506 which generates light at about 900 nm. The 900 nm light from the third layer passes through the fourth layer 508 without absorption. Finally, a portion of the near UV light that has passed through the second layer 504 and the third layer 506 is absorbed by the fourth layer 508 which produces visible light. The resulting light 509 emitted by the light source 500 has a spectrum 510 having a first peak 502 in the near UV region, a second peak 504 in the visible light region and a third peak 506 in the NIR region. It is to be understood that the light source 500 can include only a single quantum dot layer or more than two quantum dot layers, in alternate embodiments.

To calibrate the imaging device, the light from the light source (100 or 500) is transmitted onto a detector of the imaging device. The light from the light source provides a selected or predetermined intensity at various wavelength values. In particular, the light source provides light within the MR region at a selected intensity. In one embodiment, the light source generates NIR light over a wavelength spectrum from about 850 nm to about 1200 nm and having a maximal radiance at a wavelength of about 1000 nm. The sensitivity of the detector is adjusted so that the imaging device records an intensity equivalent or about the same as the selected intensity of the light source.

Figure 6:
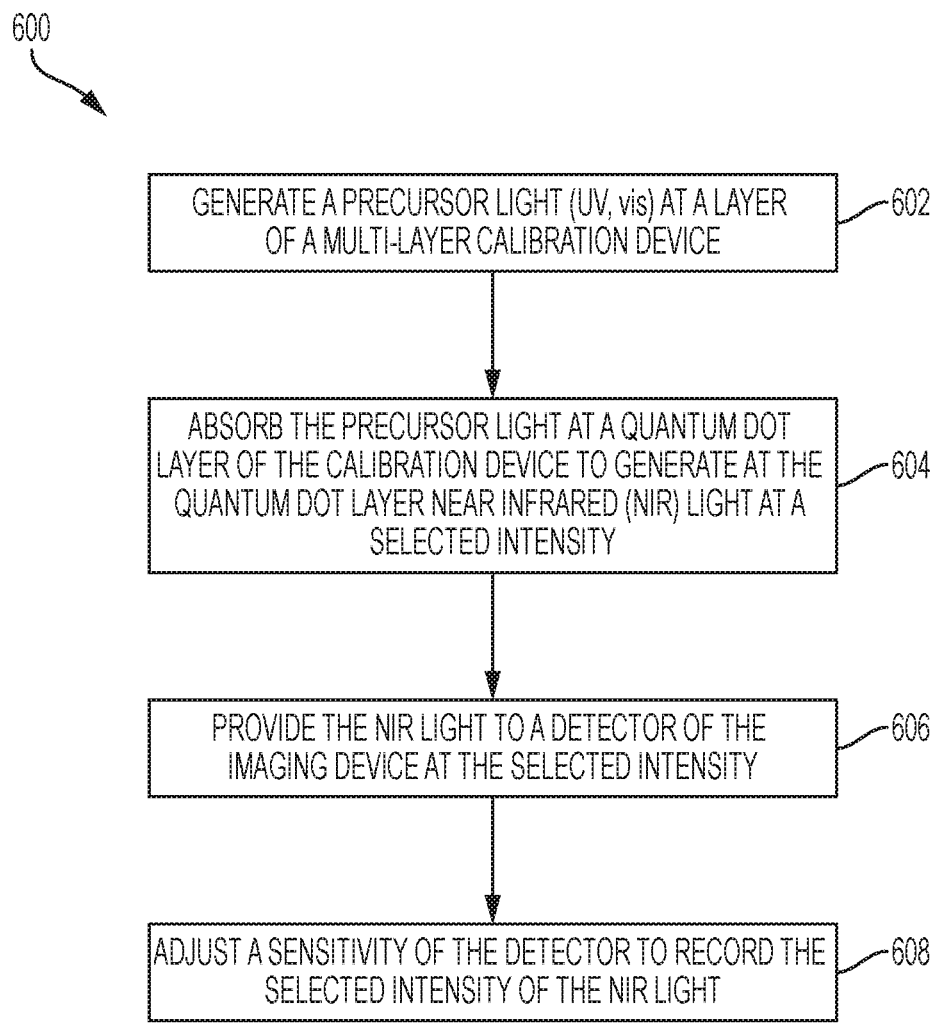
FIG. 6 shows a flowchart illustrating a process of calibrating a device such as an imaging device in one embodiment.

FIG. 6 shows a flowchart 600 illustrating a process of calibrating of a device such as an imaging device in one embodiment. In box 602, a precursor light, which can be ultraviolet light or visible light, is generated at a layer of a multi-layer light source. In box 604, a quantum dot layer of the light source absorbs the precursor light and, in response, generates near infrared light at a selected intensity. An intensity of the precursor light can be varied in order to provide the selected intensity for the near infrared light. In box 606, the NIR light is provided to a detector of the imaging device. In box 608, a sensitivity of the detector is adjusted so that the intensity of the MR light recorded by the detector is the same as the intensity of the NIR light provided by the light source.

Therefore, in one aspect of the invention, a method of calibrating an imaging device is disclosed. The method includes: generating ultraviolet light at an ultraviolet light layer of a multi-layer light source; absorbing a portion of the ultraviolet light at a quantum dot layer of the multi-layer light source, wherein the quantum dot layer generate near infrared light at a selected intensity; receiving the near infrared light at the selected intensity at the imaging device; and altering a sensitivity of the imaging device to detect the near infrared light at the selected intensity provided by the light source. The method further includes generating the ultraviolet light via a light emitting diode of the ultraviolet layer. In one embodiment, the light source includes a phosphor layer between the ultraviolet light layer and the quantum dot layer, wherein the phosphor layer absorbs a portion of the ultraviolet light to generate visible light. The quantum dot layer absorbs the visible light and generates the near infrared light in response to the absorbed visible light. In another embodiment, the light source further includes a phosphor layer with the quantum dot layer between the ultraviolet layer and the phosphor layer, wherein the phosphor layer receives a portion of the ultraviolet light that passes through the quantum dot layer and generating visible layer at the phosphor layer in response to the received ultraviolet light. In various embodiments, the quantum dot layer includes at least one of lead sulfide (PbS) quantum dots, lead selenide (PbSe) quantum dots, Cadmium Sulfide (CdS) quantum dots, or Cadmium-Tellerium-Selenide (CdTeSe) quantum dots. Light generated by the lights source is in the near infrared region over a wavelength spectrum from about 850 nm to about 1200 nm and has a maximal radiance at a wavelength of about 1000 nm.

In another aspect of the invention, a light source is disclosed, the light source including: an ultraviolet light layer that, in operation, generates ultraviolet light; and a quantum dot layer that absorbs the ultraviolet light and, in response, generates radiation within the near infrared region at a selected intensity. The ultraviolet light layer includes one or more light emitting diodes that generate the ultraviolet light. In one embodiment, the light source further includes a phosphor layer between the ultraviolet light layer and the quantum dot layer that absorbs a portion of the ultraviolet light to generate visible light. The quantum dot layer absorbs the visible light and, in response, generates the near infrared light. In another embodiment, the light source includes a phosphor layer with the quantum dot layer between the ultraviolet layer and the phosphor layer, wherein the phosphor layer absorbs a portion of the ultraviolet light that passes through the quantum dot layer to generate visible light. The quantum dot layer includes at least one of lead sulfide (PbS) quantum dots; lead selenide (PbSe) quantum dots; Cadmium Sulfide (CdS) quantum dots; and Cadmium-Tellerium-Selenide (CdTeSe) quantum dots.

In another aspect of the invention, a calibration device is disclosed. The calibration device includes: an ultraviolet light layer that, in operation, generates ultraviolet light; and a quantum dot layer that absorbs the ultraviolet light and, in response, generates radiation within the near infrared region at a selected intensity. The ultraviolet light layer includes one or more light emitting diodes that generate the ultraviolet light. In one embodiment, the calibration device further comprises a phosphor layer between the ultraviolet light layer and the quantum dot layer that absorbs a portion of the ultraviolet light to generate visible light. The quantum dot layer absorbs the visible light and, in response, generates the near infrared light. In another embodiment, the calibration device includes a phosphor layer with the quantum dot layer between the ultraviolet layer and the phosphor layer, wherein the phosphor layer absorbs a portion of the ultraviolet light that passes through the quantum dot layer to generate visible light. The calibration device of claim 16, wherein the quantum dot layer includes at least one of: lead sulfide (PbS) quantum dots, lead selenide (Pb Se) quantum dots, Cadmium Sulfide (CdS) quantum dots, and (iv) Cadmium-Tellerium-Selenide (CdTeSe) quantum dots. The calibration device generates light having a wavelength spectrum from about 850 nm to about 1200 nm and having a maximal radiance at a wavelength of about 1000 nm.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method of calibrating an imaging device, comprising:
   generating ultraviolet light at an ultraviolet light layer of a multi-layer light source;
   absorbing a portion of the ultraviolet light at a quantum dot layer of the multi-layer light source, wherein the quantum dot layer generate near infrared light at a selected intensity;
   receiving the near infrared light at the selected intensity at the imaging device; and
   altering a sensitivity of the imaging device to detect the near infrared light at the selected intensity provided by the light source.

2. The method of claim 1, further comprising generating the ultraviolet light via a light emitting diode of the ultraviolet layer.

3. The method of claim 1, wherein the light source further comprises a phosphor layer between the ultraviolet light layer and the quantum dot layer, further comprising absorbing a portion of the ultraviolet light the phosphor layer to generate visible light.

4. The method of claim 3, further comprising absorbing the visible light at the quantum dot layer and generating the near infrared light at the quantum dot layer in response to the absorbed visible light.

5. The method of claim 1, wherein the light source further comprises a phosphor layer with the quantum dot layer between the ultraviolet layer and the phosphor layer, further comprising receiving, at the phosphor layer, a portion of the ultraviolet light that passes through the quantum dot layer and generating visible layer at the phosphor layer in response to the received ultraviolet light.

6. The method of claim 4, wherein the quantum dot layer includes at least one selected from the group consisting of: (i) lead sulfide (PbS) quantum dots; (ii) lead selenide (PbSe) quantum dots; (iii) Cadmium Sulfide (CdS) quantum dots; and (iv) Cadmium-Tellerium-Selenide (CdTeSe) quantum dots.

7. The method of claim 1, further comprising generating the near infrared region over a wavelength spectrum from about 850 nm to about 1200 nm and having a maximal radiance at a wavelength of about 1000 nm.

8. A light source, comprising:
   an ultraviolet light layer that, in operation, generates ultraviolet light;
   a quantum dot layer that absorbs the ultraviolet light and, in response, generates radiation within the near infrared region at a selected intensity; and
   a phosphor layer between the ultraviolet light layer and the quantum dot layer that absorbs a portion of the ultraviolet light to generate visible light.

9. The light source of claim 8, wherein the ultraviolet light layer includes one or more light emitting diodes that generate the ultraviolet light.

10. The light source of claim 8, wherein the quantum dot layer absorbs the visible light and, in response, generates the near infrared light.

11. The light source of claim 8, further comprising a phosphor layer with the quantum dot layer between the ultraviolet layer and the phosphor layer, wherein the phosphor layer absorbs a portion of the ultraviolet light that passes through the quantum dot layer to generate visible light.

12. The light source of claim 10, wherein the quantum dot layer includes at least one selected from the group consisting of: (i) lead sulfide (PbS) quantum dots; (ii) lead selenide (PbSe) quantum dots; (iii) Cadmium Sulfide (CdS) quantum dots; and (iv) Cadmium-Tellerium-Selenide (CdTeSe) quantum dots.

13. A calibration device, comprising:
   an ultraviolet light layer that, in operation, generates ultraviolet light;
   a quantum dot layer that absorbs the ultraviolet light and, in response, generates radiation within the near infrared region at a selected intensity; and
   a phosphor layer between the ultraviolet light layer and the quantum dot layer that absorbs a portion of the ultraviolet light to generate visible light.

14. The calibration device of claim 13, wherein the ultraviolet light layer includes one or more light emitting diodes that generate the ultraviolet light.

15. The calibration device of claim 13, wherein the quantum dot layer absorbs the visible light and, in response, generates the near infrared light.

16. The calibration device of claim 13, further comprising a phosphor layer with the quantum dot layer between the ultraviolet layer and the phosphor layer, wherein the phosphor layer absorbs a portion of the ultraviolet light that passes through the quantum dot layer to generate visible light.

17. The calibration device of claim 13, wherein the quantum dot layer includes at least one selected from the group consisting of: (i) lead sulfide (PbS) quantum dots; (ii) lead selenide (PbSe) quantum dots; (iii) Cadmium Sulfide (CdS) quantum dots; and (iv) Cadmium-Tellerium-Selenide (CdTeSe) quantum dots.

18. The calibration device of claim 13, wherein the light from the calibration device includes light having a wavelength spectrum from about 850 nm to about 1200 nm and having a maximal radiance at a wavelength of about 1000 nm.

* * * * *